United States Patent [19]

Miura et al.

[11] Patent Number: 5,089,655
[45] Date of Patent: Feb. 18, 1992

[54] INDIVIDUAL α-FORM PARTICLE CRYSTALS OF TETRAKIS(3-(3,5-DI-T-BUTYL-4-HYDROXY-PHENYL)PROPIONYLOXYMETHYL)METHANE AND PROCESS FOR ITS PRODUCTION

[75] Inventors: Takanori Miura, Fukuoka; Masanori Kohara; Kunihide Oka, both of Nakatsu, all of Japan

[73] Assignee: Yoshitomi Pharmaceutical Industries, Ltd., Osaka, Japan

[21] Appl. No.: 403,492

[22] Filed: Sep. 6, 1989

[30] Foreign Application Priority Data

Sep. 7, 1988 [JP]  Japan ................................ 63-223997
Mar. 8, 1989 [JP]  Japan ................................... 1-57353

[51] Int. Cl.$^5$ ............................................. C07C 69/76
[52] U.S. Cl. ........................................................ 560/75
[58] Field of Search .......................................... 560/75

[56] References Cited

U.S. PATENT DOCUMENTS

| | | | |
|---|---|---|---|
| 3,644,482 | 2/1972 | Dexter et al. | 260/473 R |
| 3,657,322 | 4/1972 | Dexter et al. | 260/473 S |
| 3,962,313 | 6/1976 | Dexter et al. | 260/473 S |
| 4,405,807 | 9/1983 | Hasui et al. | 560/75 |
| 4,547,585 | 10/1985 | Yamanaka et al. | 560/75 |
| 4,618,700 | 10/1986 | Gubler et al. | 560/67 |
| 4,739,102 | 4/1988 | Tokunaga | 560/75 |
| 4,885,382 | 12/1989 | Gohbayashi et al. | 560/75 |

FOREIGN PATENT DOCUMENTS

| | | |
|---|---|---|
| 244361 | 11/1987 | European Pat. Off. . |
| 2201846 | 9/1987 | Japan . |
| 1081789 | 8/1967 | United Kingdom . |
| 1103145 | 2/1968 | United Kingdom . |

Primary Examiner—Paul J. Killos
Attorney, Agent, or Firm—Wenderoth, Lind & Ponack

[57] ABSTRACT

Novel individual α-form particle crystals of tetrakis[3-(3,5,-di-t-butyl-4-hydroxyphenyl)propionyloxymethyl]methane and process for its production are disclosed.

9 Claims, 6 Drawing Sheets

INDIVIDUAL α-FORM PARTICLE CRYSTALS OF TETRAKIS(3-(3,5-DI-T-BUTYL-4-HYDROXY-PHENYL)PROPIONYLOXYMETHYL)METHANE AND PROCESS FOR ITS PRODUCTION

BACKGROUND OF THE INVENTION

This invention relates to novel individual particle crystals of tetrakis[3-(3,5-di-t-butyl-4-hydroxyphenyl)-propionyloxymethyl]methane (hereinafter sometimes referred to as Compound-A) in a α-crystal form which is useful as an antioxidant for polyolefins and the like. In further detail, it relates to individual particle crystals of Compound-A having α-crystal form, comprising crystals in substantially cubic or rectangular parallelepipedal shape or aggregates thereof.

The products of Compound-A marketed presently have critical deflects in workability, measurability and environmental hygiene since they are inferior in powder-properties, for example, in that they are in the fine powder form, of low bulk density and of inferior fluidity and easily scatter and drift in handling. Therefore, improvement is desired.

Compound-A has a property crystallographically called multiple forms, which means that it has various stable or semi-stable crystal forms representable by the same chemical structure. Heretofore, there have been known several crystal forms defined as α-form, β-form, γ-form, δ-form and the like. The above-mentioned marketed products are in the β-crystal forms. There is close relationship between the respective crystal forms and the purity and powder property (micromeritical property) of Compound-A. By a variety of methods, the objective crystal forms can be obtained.

Hitherto, there have been presented proposals for improving the defects of the marketed products by preparing Compound-A in particular crystal forms or by obtaining Compound-A by combination of a particular crystal form with a particular particle form. For example, (1) in the official gazette publications of Japanese Patent Applications Publication (Kokoku) Nos. 13018/1985 and 13017/1985, the powder property, which is a defect of α-crystal and the marketed β-crystal, is improved by obtaining Compound-A in the δ-form which is a semi-stable crystal form and (2) in the official gazette publication of Japanese Patent Application Laid-open (Kokai) No. 258343/1987, are improved the defects of the marketed products by obtaining Compound-A in individual particle crystal forms by recrystallizing under special conditions, though in the same semi-stable β-form as the form of the marketed products.

On the other hand, the crystals in the α-form which belongs to the stable crystal forms, can be obtained by recrystallization from a solvent such as n-heptane, n-hexane or methanol as disclosed in the offical gazette publications of Japanese Patent Applications Publication (Kokoku) Nos. 18617/1967 and 19083/1967, Japanese Patent Application Laid-open (Kokai) No. 156645/1985 and so on. However, the case is that these crystals are the most inferior both in purity and in powder property, and therefore are less valuable products.

As mentioned above, the heretofore proposed methods for improvement relate to preparing Compound-A in the δ-form and in the individual particle β-form, both of which are unstable crystal forms, avoiding the α-form which is inferior in purity and powder property, for the purpose of obtaining Compound-A having superior powder property. These methods, however, cannot be looked upon as economical in that the number of steps is increased and a large amount of impurity is allowed to exist.

That is, according to the methods of Japanese Patent Applications Publication (Kokoku) Nos. 13017/1985 and 13018/1985, in the ester interchange reaction, it is necessary to add a dicarboxylic acid ester of the formula (1)

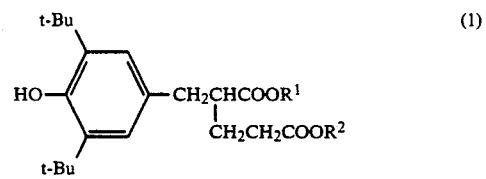

wherein $R^1$ and $R^3$ respectively stand for an alkyl group having 1-6 carbon atoms and it is also necessary to isolate the molecular adduct of Compound-A with isopropanol, which results in the increase in the number of the steps. Thus, the methods are not economical. In the method of Japanese Patent Application Kokai No. 258343 1987, it is necessary to allow methyl or ethyl 3-(3,5-di-t-butyl-4-hydroxyphenyl)propionate, which is a starting compound, and the tris-substituted compound of the formula (2)

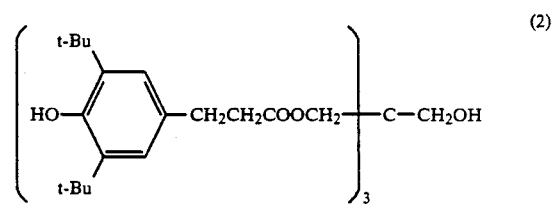

which is an intermediate compound resulting from incomplete reaction, to be contained in a large amount before purification by recrystallization (as described in the specification, when the content of the objective Compound-A is too high at the completion of the reaction, it is required to add the starting compound or the tris-substituted compound (2) and purposely mix them therewith). Thus, the obtained products tend to have reduced purity and also the yield of the recrystallization is lowered, and the method is not an economical one.

SUMMARY OF THE INVENTION

The object of this invention is to provide Compound-A having high purity and excellent powder property in an α-crystal form which belongs to stable crystal forms, that is, α-form crystals of Compound-A in individual particle forms, comprising crystals in substantially cubic or rectangular parallelepipedal shape or aggregates thereof.

Another object of this invention is to provide a process for the production of such individual α-form crystals of Compound-A as mentioned hereinbefore.

DETAILED DESCRIPTION

The present inventors have conducted intensive studies on the crystal forms of Compound-A, particularly the α-forms to find an α-form Compound-A which has good powder property and novel particle form different from that of the hitherto-known α-form, which culminated in the completion of the present invention.

This invention relates to tetrakis[3-(3,5-di-t-butyl-4-hydroxyphenyl)propionyloxymethyl]methane in individual α-form particle crystal forms, comprising individual α-form particle crystals in substantially cubic or rectangular parallelepipedal shape and aggregates thereof, which can be obtained by recrystallization from an aliphatic saturated hydrocarbon having 8-10 carbon atoms alone or a mixture thereof with a small amount of methanol as the recrystallization solvent of tetrakis[3-(3,5-di-t-butyl-4-hydroxyphenyl)propionylmethyl]methane which can be prepared by subjecting methyl 3-(3,5-di-t-butyl-4-hydroxyphenyl)propionate and pentaerythritol to ester interchange reaction, or the marketed product thereof.

As specific examples of the aliphatic saturated hydrocarbon having 8-10 carbon atoms to be used as the solvent, mention is made of Iso-Par (Exxon Chemical's commercial product name), Shellsol (Shell Chemical's commercial product name), IP Solvent (Idemitsu Chemical's commercial product name) and so on. When methanol is added, it is added preferably in a proportion of 1 to 4% by weight relative to the amount of said solvent. The content of Compound-A before crystallization is about 85 to about 98%. The crystallization temperature is in the range from 70° C. to 20° C.

The α-form Compound-A in individual particle forms of the present invention comprises the crystal particles having a crystal particle diameter of not more than 0.1 mm in a proportion of not more than 5% by weight, and more preferably, it has the following homogenous crystal particle size distribution:

the crystal particles of a crystal particle diameter of more than 1 mm share no more than 1% by weight;

the crystal particles of a crystal particle diameter ranging from 0.1 to 1 mm share no less than 94% by weight; and the crystal particles of a crystal particle diameter below 0.1 mm share no more than 5% by weight.

FUNCTION

Figure 1:
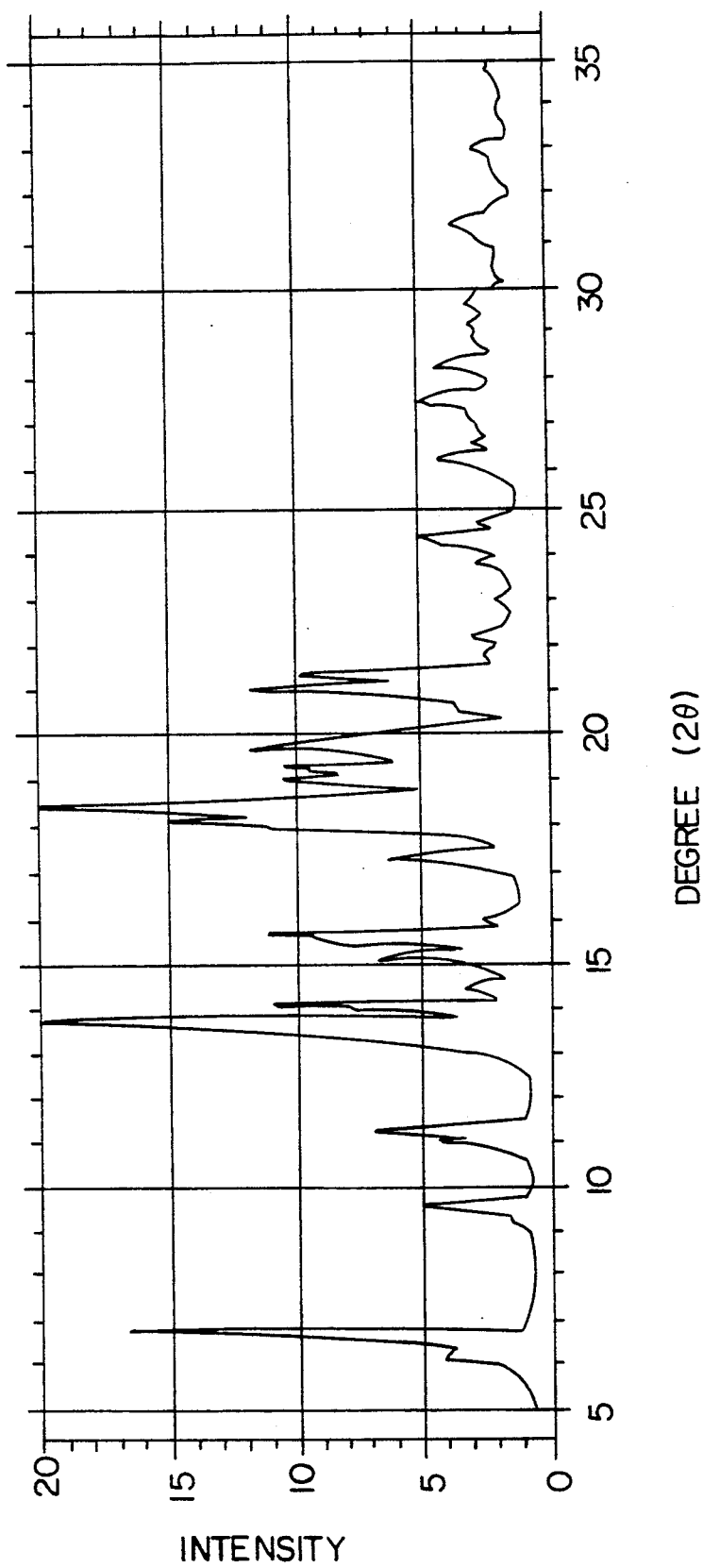
FIG. 1 shows the X-ray diffraction spectrum of the compound of the present invention as obtained in accordance with Example 1.
Figure 5:
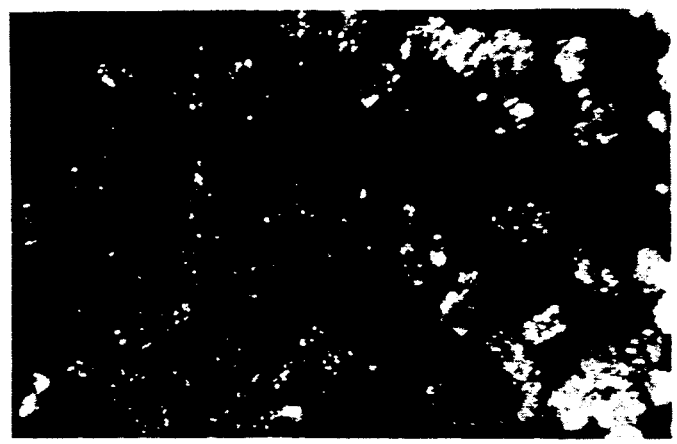
FIG. 5 shows the microscopic photograph of the α-form crystals in individual particle form as obtained in accordance with the present invention.
Figure 6:
FIG. 6 shows the microscopic photograph of the α-form crystals as obtained by the hitherto-known method.

From the X-ray (Cu - Kα) diffraction spectrum as shown in FIG. 1 and the melting point of 122°-124° C., the Compound-A obtainable according to the present invention is deemed to have a crystal structure in the α-form. As shown in the microscopic photograph in FIG. 5, it comprises crystal particles in substantially cubic or rectangular parallelepipedal shape and aggregates thereof, and it comprises only a little amount of fine powders. From the foregoing, the Compound-A of the present invention has a particle form definitely distinguishable from the α-form crystals obtained by the hitherto known method as shown in the microscopic photograph in FIG. 6.

Besides, since the α-form crystals of Compound-A obtained in accordance with the present invention, unlike the hitherto-known crystals in the α-form, are in substantially individual particle forms, they bear characteristics of excellent powder property in the following respects: they can be easily purified by recrystallization; the particle size distribution is homogeneous; the diversity of the particle size distribution is narrow; the bulk density is high; they are not so easily pulverized in drying and transportation and the like. Therefore, they are extremely advantageous in that working efficiency and working environment is improved. Thus, the Compound-A in the α-form of the present invention has high purity and excellent powder property which the hitherto-known α-form fails to have, and is easily produced.

Below, the present invention is specifically described by examples, but the present invention is not limited thereto.

EXAMPLE 1

Figure 2:
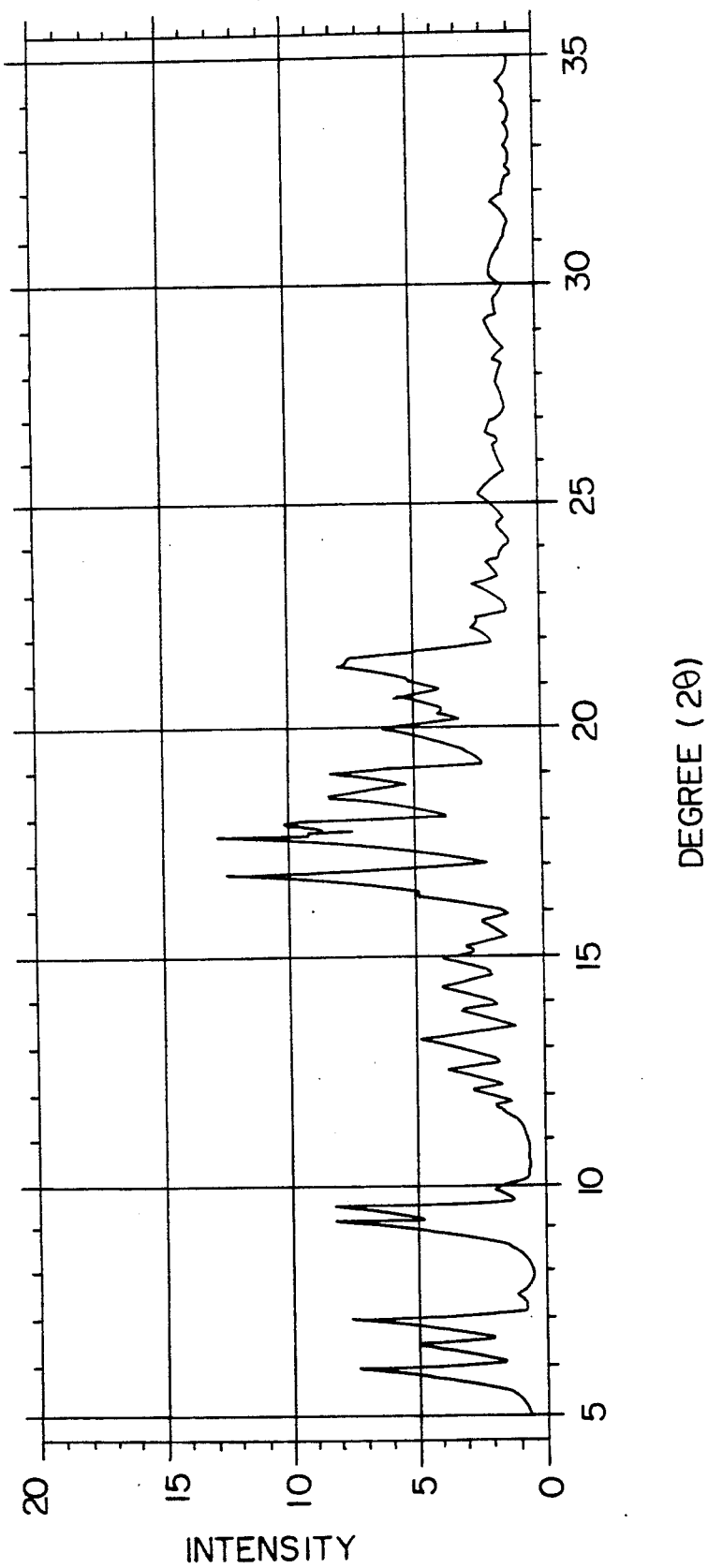
FIG. 2 shows the X-ray diffraction spectrum of the marketed product as used in Example 1.
Figure 7:
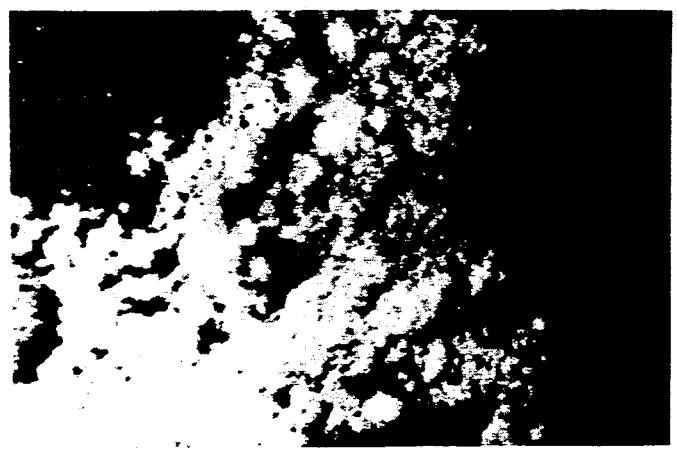
FIG. 7 shows the microscopic photograph of the marketed product.

In a 500 ml-four-mouthed flask were put 150 g of marketed tetrakis[3-(3,5-di-t-butyl-4-hydroxyphenyl)-propionyloxymethyl]methane (This product is in the form of fine powders as shown in the microscopic photograph in FIG. 7, and it has m.p. of 112°-114° C. and the β-form crystal structure as shown in the X-ray diffraction spectrum in FIG. 2.) and 180 g of Iso-Par E (a solvent of an aliphatic saturated hydrocarbon of 8-10 carbon atoms marketed by Exxon Chemical , and the mixture was heated to 95° C. to be completely dissolved. The mixture was gradually cooled under stirring, and at 70° C., a small quantity of crystals in the α-form was added as the seed crystals. When the mixture had been stirred at 60°-50° C. for 4 hours, most of the crystals deposited. Further, the mixture was cooled to 30° C. for the completion of crystallization. The resulting slurry was filtered by sunction-filtration and dried to give 146 g of white crystals of high fluidity. The melting point of 122°-124° C. and X-ray diffraction spectrum as shown in FIG. 1 confirmed that the crystals were in the α-form.

The characteristics of the obtained crystals as compared with those of the crystals in the α-form of the marketed product and those of the crystals obtained by the conventional method are tabulated in Table 1.

EXAMPLE 2

By conducting the same procedure as that in Example 1 except that 3.7 g of methanol was additionally added for dissolution, 145 g of white crystals having excellent fluidity was obtained. The melting point of 122°-124° C. and the X-ray diffraction spectrum confirmed that the crystals were in the α-form.

EXAMPLE 3

A 1 l-four-mouthed flask equipped with a stirrer, a reflux-condenser, a thermometer and pressure reduction-adjusting valve was charged with 479.5 g of methyl 3-(3,5-di-t-butyl- 4-hydroxyphenyl)propionate, 54.5 g of pentaerythritol and 0.25 g of dibutyltin oxide, and the mixture was reacted at 195° C. under atmospheric pressure for 2 hours and methanol resulting as by-product was distilled off. The mixture was reacted at 195° C. under reduced pressure of 40 mmHg for 2 hours and further at 195° C. under reduced pressure of 2-5 mmHg for 12 hours, and methanol resulting as the by-product was distilled off for the completion of the reaction. The weight of the reaction mixture was 483 g after the pressure was enhanced to the atmospheric pressure, and the reaction mixture was found to contain the objective compound in an amount of 89% from the result of the analysis by HPLC.

Figure 3:
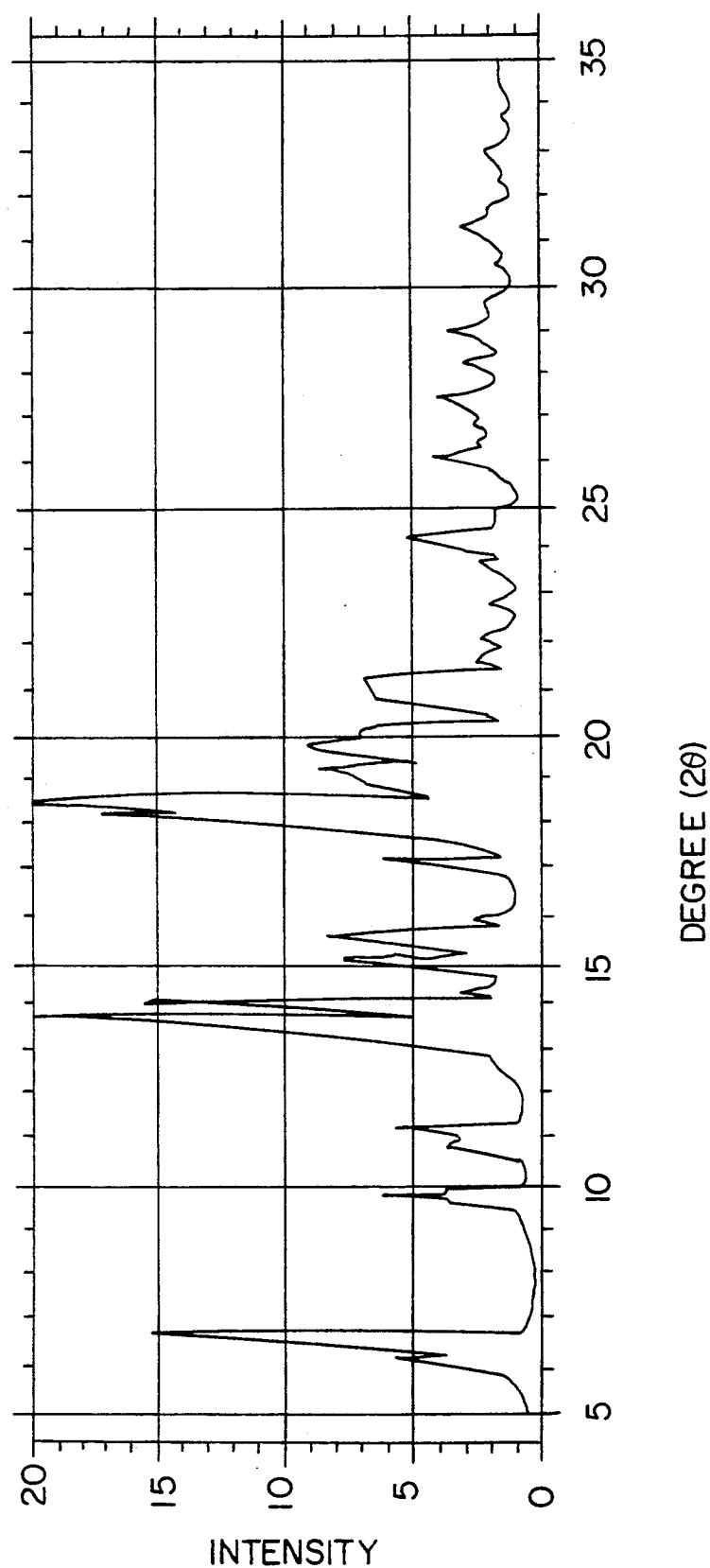
FIG. 3 shows the X-ray diffraction spectrum of the compound of the present invention as obtained in accordance with Example 3.

In a 500 ml-four-mouthed flask were put 150 g of the reaction mixture, 170 g of Iso-Par E and 6.2 g of methanol, and the mixture was heated to 85° C. to give a homogeneous solution. Thereafter, the mixture was gradually cooled and at 55° C., a small amount of seed crystals in the α-form was added. The mixture was allowed to be crystallized at 50°-45° C. for 8 hours, and then cooled to 25° C. for the completion of the crystallization. The crystals were collected by filtration, washed with 100 g of cooled Iso-Par E and dried to give 126 g of white crystals of high fluidity. The melting point of 122°-124° C. and the X-ray diffraction spectrum as shown in FIG. 3 confirmed that these crystals were in the α-form.

COMPARATIVE EXAMPLE 1

Figure 4:
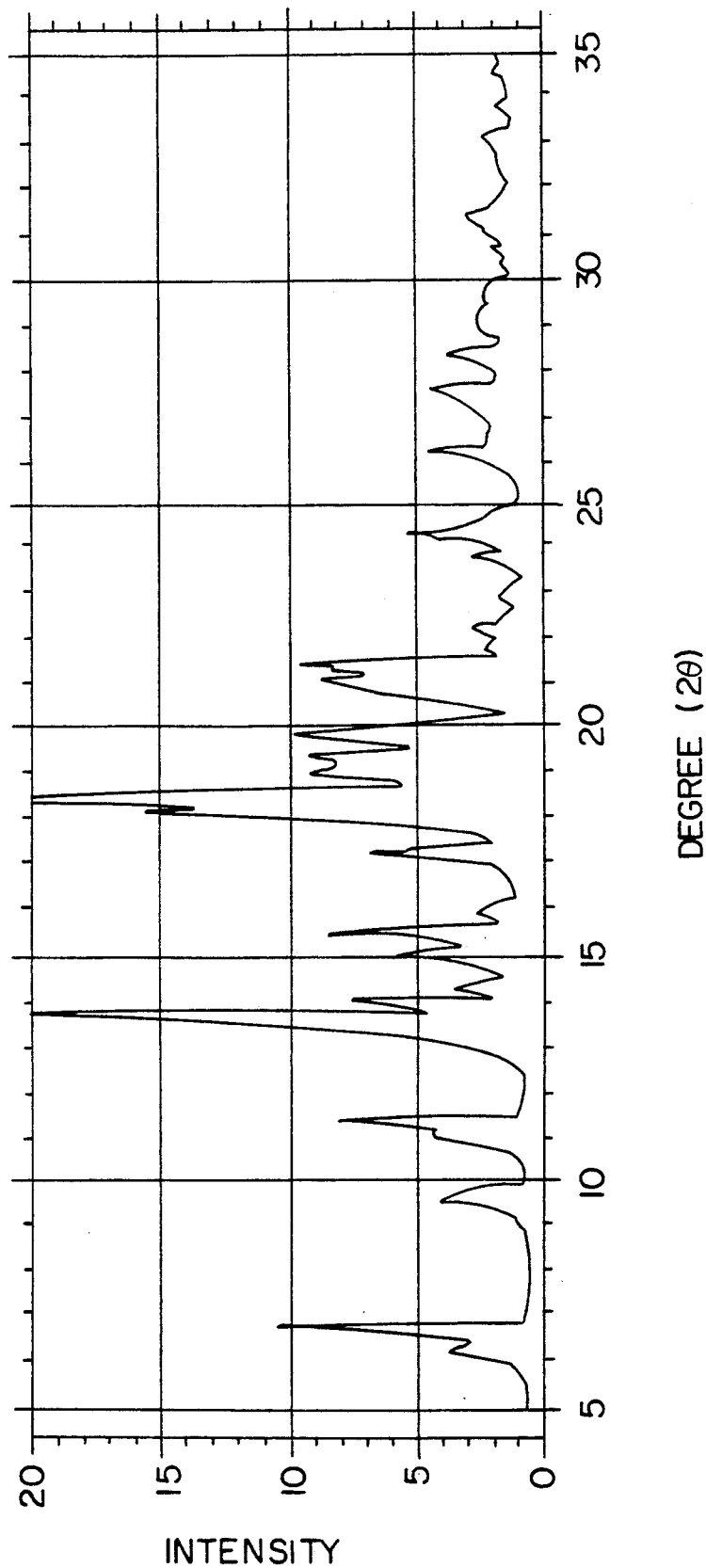
FIG. 4 shows the X-ray diffraction spectrum of the compound as obtained in accordance with comparative Example 1.

Using 150 g of the reaction product as obtained in Example 3 and 170 g of methanol as used in Example 1 of Japanese Patent Application Kokai No. 156645/1985 instead of Iso-Par E used in Example 3, after heating to 60° C. to obtain a homogeneous solution, crystallization was conducted in the same manner as that described in Example 3. The obtained crystals were washed with 100 ml of cool methanol and dried to give 120 g of white powders. The melting point (122°-124° C.) and the X-ray diffraction spectrum as shown in FIG. 4 confirmed that these crystals were in the α-form.

COMPARATIVE EXAMPLE 2

By conducting the same procedure as in Comparative Example 1 using n-heptane which is used in Example 2 of Japanese Patent Application Publication (Kokoku) No. 18617/1967 instead of methanol in Comparative Example 1, 118 g of pale yellow powders was obtained. The melting point and X-ray diffraction spectrum confirmed that these powders were α-form crystals.

COMPARATIVE EXAMPLE 3

By conducting the same procedure as in Comparative Example 1 except that the crystallization temperature was changed to 40° C. and n-hexane as used in Example 1 of Japanese Patent Application Publication (Kokoku) No. 19083/1967 was used instead of methanol in Comparative Example 1, 125 g of pale yellow powders was obtained. The melting point and X-ray diffraction spectrum confirmed that these powders were α-form crystals.

TEST EXAMPLE 1

Figure 8:
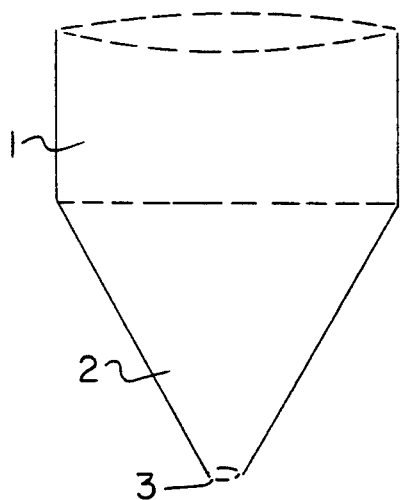
FIG. 8 shows the hopper as used for the measurement of the falling velocity (1 indicates the cylinder section, 2 indicates the conic section and 3 indicates the outlet of the sample).

The characteristics of the crystals of Examples 1-3, Comparative Examples 1-3 and the marketed product are tabulated in Table 1. The bulk density and angle of repose were measured a powder tester (manufactured by Hosokawa Micron). The falling velocity was obtained by measuring the falling velocity from the stainless steel hopper as shown in FIG. 8, (wherein the diameter of the cylinder section 1 is 83 mm, the diameter of outlet 3 is 8 mm, and the height of the conic section 2 is 65 mm) the less the value is, the higher the fluidity. The marketed product was one manufactured by Ciba-Geigy Corporation.

TABLE 1

|  | Example 1 | Example 2 | Example 3 | Comparative Example 1 | Comparative Example 2 | Comparative Example 3 | Marketed Product |
|---|---|---|---|---|---|---|---|
| Recrystallization solvent | Iso-Par E | Iso-Par E Methanol | Iso-Par E Methanol | Methanol | n-heptane | n-hexane | — |
| Appearance | White crystals | White crystals | White crystals | White crystals | Pale-yellow powder | Pale-yellow powder | White powder |
| HPLC purity (%) | 98.0 | 97.0 | 96.1 | 96.5 | 95.2 | 94.6 | 97.0 |
| m.p. (°C.) | 122-124 | 122-124 | 122-124 | 122-125 | 118-122 | 116-122 | 113-114 |
| Crystal form | α | α | α | α | α | α | β |
| Bulk density (g/ml) | 0.54 | 0.55 | 0.46 | 0.28 | 0.30 | 0.33 | 0.35 |
| Angle of repose (°) | 40 | 40 | 46 | 48 | 51 | 51 | 50 |
| Falling velocity (sec./100 ml) | 11 | 12 | 13 | 95 | 185 | 200 | 210 |
| Particle size distribution (%) | | | | | | | |
| >1 mm | 0 | 0.2 | 0 | 4.3 | 0 | 0 | 0.1 |
| 1.0-0.50 mm | 0.2 | 0.2 | 1.6 | 4.4 | 5.4 | 6.8 | 0.1 |
| 0.50-0.25 mm | 61.9 | 6.4 | 1.2 | 18.1 | 15.6 | 18.2 | 14.1 |
| 0.25-0.10 mm | 37.8 | 90.1 | 93.1 | 69.7 | 45.3 | 45.7 | 53.7 |
| <0.1 mm | 0.1 | 3.1 | 3.8 | 2.9 | 32.7 | 29.3 | 32.0 |

TEST EXAMPLE 2

The mechanical strength of the crystal particles of Compound-A obtained in Example 2 was tested by shaking-stirring method. The sample (100 g) was put in a 1000 ml-flask, which was shaken for 7 hours, and the results of the particle size distribution before and after the test are shown in Table 2. From the fact that there is little difference between the particle size distribution before and after the test, it is shown that the mechanical strength of the crystal particles is high.

TABLE 2

| Particle size | Before shaking | After shaking |
|---|---|---|
| >1 mm | 0.2% | 0% |
| 1.0-0.5 mm | 0.2% | 2.2% |
| 0.5-0.25 mm | 6.4% | 11.5% |
| 0.25-0.10 mm | 90.1% | 81.6% |
| <0.1 mm | 3.1% | 4.7% |

We claim:

1. Tetrakis [3-(3,5-di-t-butyl-4-hydroxyphenyl)propionyloxymethyl]methane in individual particle crystal forms, comprising individual α-form crystals in substantially cubic or rectangular parallelepipedal shape and aggregates thereof.

2. A compound as claimed in claim 1, wherein the crystal particles having a crystal particle diameter of not more than 0.1 mm share no more than 5% by weight.

3. A compound as claimed in claim 1, wherein the crystal particle size distribution is as follows:
   the crystal particles of a crystal particle diameter of more than 1 mm share no more than 1% by weight;
   the crystal particles of a crystal particle diameter ranging from 0.1 to 1 mm share no less than 94% by weight;
   and the crystal particles of a crystal particle diameter below 0.1 mm share no more than 5% by weight.

4. A compound as claimed in claim 1, wherein the crystals are pulverized.

5. A process for the production of tetrakis[-(3,5-di-t-butyl-4-hydroxyphenyl)propionyloxymethyl]methane in individual α-form particle crystal forms comprising crystals in substantially cubic or rectangular pallarelepipedal and aggregates thereof, which comprises crystallizing tetrakis[3-(3,5-di-t-butyl-4-hydroxyphenyl)propionyloxymethyl]-methane from an aliphatic saturated hydrocarbon having 8-10 carbon atoms or a mixture thereof with a small amount of methanol as the crystallization solvent.

6. A process as claimed in claim 5 wherein the crystallization solvent is a mixture containing 1-4% by weight of methanol relative to the amount of the aliphatic saturated hydrocarbon having 8-10 carbon atoms.

7. A process as claimed in claim 5 wherein the content of tetrakis[3-(3,5-di-t-butyl-4-hydroxyphenyl)propionyloxymethyl]methane prior to crystallization is 85-98%.

8. A process as claimed in claim 5 wherein the crystallization temperature is in the range from 70°-20° C.

9. A process as claimed in claim 5 wherein the crystallization solvent is an aliphatic saturated hydrocarbon having 8-10 carbon atoms or a mixture thereof with 1-4% by weight of methanol relative to the amount of the aliphatic saturated hydrocarbon.

* * * * *